(12) United States Patent
Saito et al.

(10) Patent No.: US 8,960,908 B2
(45) Date of Patent: Feb. 24, 2015

(54) FUNDUS IMAGING APPARATUS AND CONTROL METHOD

(71) Applicant: Canon Kabushiki Kaisha, Tokyo (JP)

(72) Inventors: Yohei Saito, Chigasaki (JP); Satoshi Aikawa, Yokohama (JP); Hideyuki Ohban, Kawaguchi (JP); Yoshitaka Nakano, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/057,220

(22) Filed: Oct. 18, 2013

(65) Prior Publication Data

US 2014/0118689 A1    May 1, 2014

(30) Foreign Application Priority Data

Oct. 26, 2012 (JP) ................. 2012-237264

(51) Int. Cl.
*A61B 3/14* (2006.01)
*A61B 3/00* (2006.01)

(52) U.S. Cl.
USPC ........................... 351/206; 351/246

(58) Field of Classification Search
USPC ................................. 351/200–246
See application file for complete search history.

(56) References Cited

U.S. PATENT DOCUMENTS

| 8,449,114 B2 | 5/2013 | Ohban |
| 8,480,232 B2 | 7/2013 | Aikawa |
| 8,511,824 B2 | 8/2013 | Saito |
| 2011/0051087 A1 | 3/2011 | Inoue et al. |
| 2011/0137157 A1 | 6/2011 | Imamura et al. |
| 2011/0242484 A1 | 10/2011 | Furukawa et al. |
| 2012/0050670 A1 | 3/2012 | Nakahara et al. |
| 2012/0050671 A1 | 3/2012 | Aikawa |
| 2012/0050672 A1* | 3/2012 | Aikawa ................ 351/206 |
| 2012/0050677 A1 | 3/2012 | Ohban |
| 2012/0134563 A1 | 5/2012 | Nakano |
| 2013/0235345 A1* | 9/2013 | Ohban ................ 351/206 |
| 2013/0301005 A1 | 11/2013 | Saito |

FOREIGN PATENT DOCUMENTS

| EP | 1752084 A2 | 2/2007 |
| JP | 2011-189063 A | 9/2011 |

OTHER PUBLICATIONS

Feb. 5, 2014 European Search Report in European Patent Appln. No. 13188718.4.

* cited by examiner

*Primary Examiner* — Mohammed Hasan (74) *Attorney, Agent, or Firm* — Fitzpatrick, Cella, Harper & Scinto

(57) ABSTRACT

A fundus imaging apparatus selects a focal position detection method in accordance with whether a diopter correction lens is inserted in an optical path of an imaging optical system that includes an imaging unit; and detects a focal position based on a signal from the imaging unit according to the selected focal position detection method.

16 Claims, 6 Drawing Sheets

FUNDUS IMAGING APPARATUS AND CONTROL METHOD

BACKGROUND OF THE INVENTION

1. Field of the Invention

The present invention relates to a fundus imaging apparatus and a control method.

2. Description of the Related Art

In order to capture a suitable fundus image using a fundus camera, it is necessary to focus on the fundus of each eye individually. This is because different eyes to be examined have different degrees of refraction. A fundus camera having an autofocus function has been proposed as a camera designed to facilitate such a focusing operation. In general, when imaging the fundus of an eye, such a fundus camera performs focusing by using a focus lens placed in an observation optical system and focus indices which are driven in synchronism with the focus lens.

In this case, if a diopter correction lens for correcting strong myopia or hyperopia is inserted in the observation optical system, the optical relationship between split and focus changes. That is, if a diopter correction lens is inserted in the observation optical system, since the optical relationship between the focus lens and the focus indices deteriorates, it is impossible to perform focusing by using the focus indices. This makes it necessary for the examiner to manually perform focusing while observing an actual fundus image. Japanese Patent Laid-Open No. 2011-189063 has disclosed an invention which facilitates manual focusing operation by changing the operation sensitivity of a focus lens when a diopter correction lens is inserted.

It is however cumbersome for the examiner to perform such a manual focusing operation. The lower the degree of skill of the examiner, the more time it takes for the focusing operation. This imposes a burden on the person having their eye examined and may cause stress to the eye itself.

SUMMARY OF THE INVENTION

According to one aspect of the present invention, there is provided a fundus imaging apparatus comprising: an illumination optical system operable to project illumination light on a fundus of an eye to be examined; an imaging optical system operable to guide reflected light from the fundus to an imaging unit; a driveable focus lens which is provided in an optical path of the imaging optical system and which is operable to focus the reflected light onto the imaging unit; a focusing unit operable to detect a focal position of the reflected light based on a signal from the imaging unit and to drive the focus lens according to the detected focal position; and a selection unit operable to select a focal position detection method used by the focusing unit in accordance with whether a diopter correction lens is inserted in the optical path or not.

Also, according to another aspect of the present invention, there is provided a method of controlling a fundus imaging apparatus comprising: selecting a focal position detection method in accordance with whether a diopter correction lens is inserted in an optical path of an imaging optical system that includes an imaging unit; and detecting a focal position based on a signal from the imaging unit according to the selected focal position detection method.

Further features of the present invention will become apparent from the following description of exemplary embodiments (with reference to the attached drawings).

DESCRIPTION OF THE EMBODIMENTS

A preferred embodiment of a fundus imaging apparatus to which the present invention is applied will be described below with reference to the accompanying drawings. According to the embodiment described below, there is provided a fundus camera which can execute autofocus operation even in a state in which a diopter correction lens is inserted.

Figure 1:
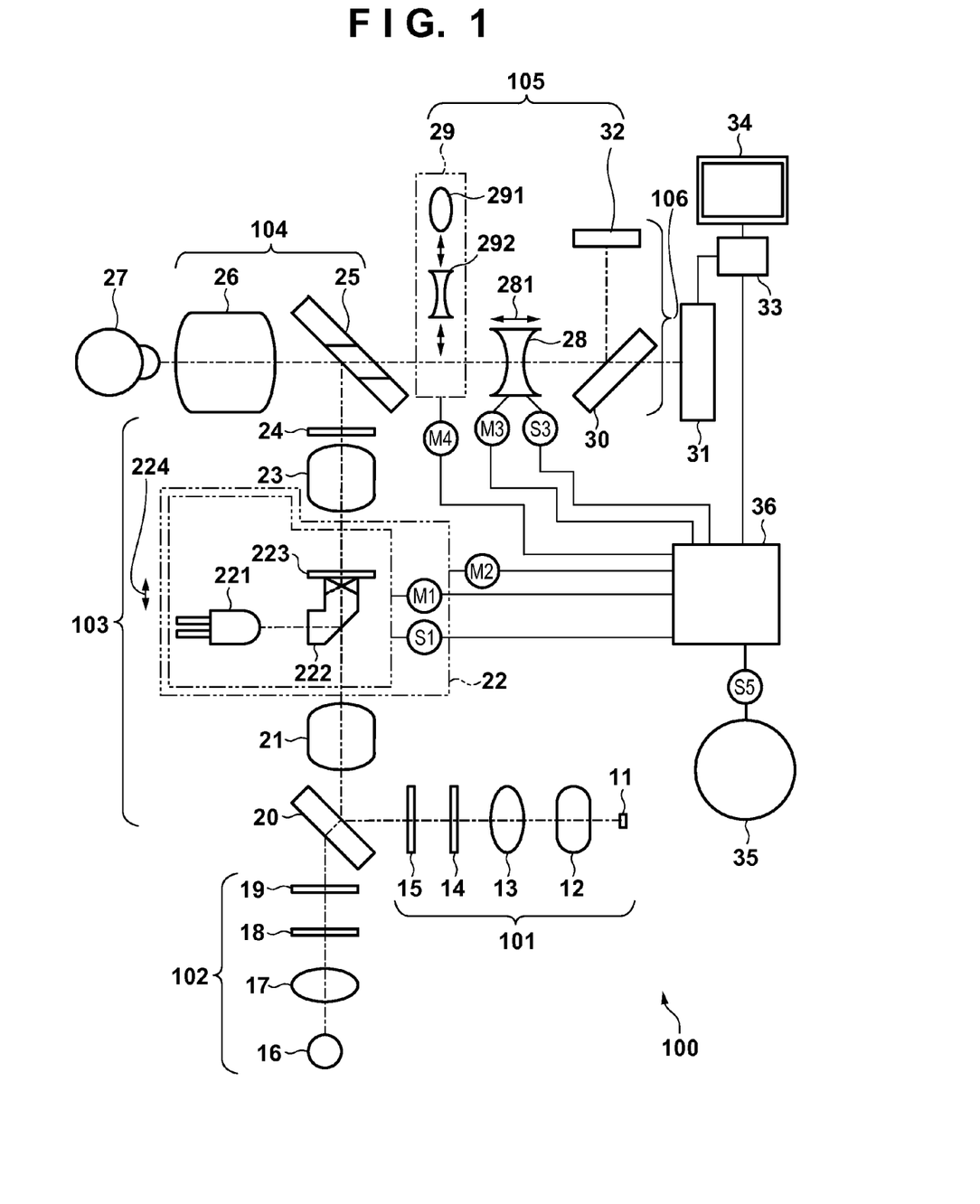
FIG. 1 is a schematic arrangement of a fundus camera according to an embodiment.

FIG. 1 shows an example of the schematic arrangement of a fundus camera 100 as a fundus imaging apparatus according to this embodiment. The fundus camera 100 includes an imaging light source part 101, an observation light source part 102, an illumination optical system 103, an imaging/illumination optical system 104, and an imaging optical system 105. The light beam emitted from the imaging light source part 101 or the observation light source part 102 illuminates the fundus region of the eye 27 through the illumination optical system 103 and the imaging/illumination optical system 104. The fundus region image is then formed on an imaging device through the imaging/illumination optical system 104 and the imaging optical system 105.

In the imaging light source part 101, reference numeral 11 denotes a light amount detection part, which is a sensor using known photoelectric conversion such as an SPC or PD (photodiode); 12, an imaging light source which emits light by applying a voltage to xenon (Xe) sealed in a glass tube and can obtain white light strong enough to record a fundus image at the time of imaging; 13, an imaging condenser lens which is a general spherical lens; 14, an imaging ring slit which is a flat plate having an annular opening; and 15, an imaging crystalline lens baffle which is also a flat panel having an annular opening.

In the observation light source part 102, reference numeral 16 denotes an observation light source which is a light source capable of continuously emitting light such as a halogen lamp or LED, and emits infrared light depending on the characteristics of the device and/or a filter; 17, an observation condenser lens which is a general spherical lens; 18, an observation ring slit which is a flat plate having an annular opening; and 19, an observation crystalline lens baffle which is also a flat panel having an annular opening.

The illumination optical system 103 relays the light beam generated by the imaging light source part 101 and the observation light source part 102 and forms index images for focusing on a fundus image. In the illumination optical system 103, reference numeral 20 denotes a dichroic mirror which transmits infrared light and reflects visible light. Therefore, the light beam of visible light generated by the imaging light source part 101 is reflected by the dichroic mirror 20. The light beam of infrared light generated by the observation light source part 102 is transmitted through the dichroic mirror 20, and guided to the illumination optical system 103. Reference numeral 21 denotes a first illumination relay lens; and 23, a second illumination relay lens. These lenses form ring illumination into an image on an eye to be examined.

Reference numeral 22 denotes a split unit which is constituted by a split LED 221 for projecting focus indices (split images), a prism 222 for splitting the light emitted from the LED 221, and a focus index mask 223 indicating the outer shape of each focus index. The split unit 22 includes a moving mechanism which shifts each focus index in the optical-axis direction by moving these components in an arrow direction 224 shown in FIG. 1 and an entering/retreating mechanism which causes these components to enter the illumination optical system 103 at the time of observation and to retreat from it at the time of imaging. Reference symbol M1 denotes a split shift driving motor; S1, a split position sensor which shifts the split unit 22 in the arrow direction 224 to focus on each focus index and to detect the stop position; and M2, a split entering/retreating driving motor which causes the split unit 22 to enter/retreat with respect to the illumination optical system 103. The split entering/retreating driving motor M2 is controlled to drive the split unit 22 to enter the illumination optical system 103 to project a split index in an observation image at the time of fundus observation. At the time of imaging, the split entering/retreating driving motor M2 is controlled to drive the split unit 22 to retreat from the illumination optical system 103 so as to prevent each focus index from being depicted in a captured image. Reference numeral 24 denotes a cornea baffle which prevents unnecessary reflected light from the cornea of the eye to be examined from being depicted in a fundus image.

The imaging/illumination optical system 104 projects an illumination light beam on the fundus of an eye 27 to be examined and guides a fundus image of the eye to be examined. In the imaging/illumination optical system 104, reference numeral 25 denotes a perforated mirror whose peripheral portion is a mirror and central portion is a hole. The light beam guided from the illumination optical system 103 is reflected by the mirror portion and illuminates the fundus of the eye to be examined through an objective lens 26. The illuminated fundus image of the eye to be examined returns to the objective lens 26 and is guided to the imaging optical system 105 through the hole in the central portion of the perforated mirror 25.

The imaging optical system 105 forms a fundus image of the eye to be examined on the imaging device upon focus adjustment. In the imaging optical system 105, reference numeral 28 denotes a focus lens which is a lens for focus adjustment of an imaging light beam passing through the central hole of the perforated mirror 25 and which performs focus adjustment by moving in an arrow direction 281 in FIG. 1. Reference symbol M3 denotes a focus lens driving motor; S3, a focus lens position sensor which performs focusing by driving the focus lens 28 and detects its stop position. Reference numeral 29 denotes a diopter correction lens which is retractably placed on the optical axis to focus on the fundus of the eye to be examined which has strong myopia or hyperopia which is difficult to focus on with a focus lens. The diopter correction lens 29 includes a positive diopter correction lens 291 which is a convex lens and a negative diopter correction lens 292 which is a concave lens. Reference numeral M4 denotes a diopter correction lens entering/retreating driving motor which causes the negative diopter correction lens 292 to enter/retreat (for insertion/removal) with respect to the imaging optical system 105 if the patient has strong myopia and causes the positive diopter correction lens 291 to enter/retreat with respect to the imaging optical system 105 if the patient has strong hyperopia.

Reference numeral 31 denotes an imaging device which photoelectrically converts imaging light; 33, an image processing part which outputs the signal output from the imaging device 31 to a monitor 34 and a system control part 36. In an internal fixation lamp part 106, a half mirror 30 branches an optical path from the imaging optical system 105, and an internal fixation lamp unit 32 faces the optical path. The internal fixation lamp unit 32 is constituted by a plurality of LEDs and turns on an LED at a position corresponding to the visual fixation part selected by the examiner. By letting the patient whose eye is being examined fix his/her vision to the turned-on LED, the examiner can obtain a fundus image in a desired direction.

A focusing operation member 35 is an operation member used for focusing operation by the examiner. A focusing operation member position sensor S5 detects the stop position of the focusing operation member 35 and outputs the detected position to the system control part 36. Note that in the fundus camera 100, signals from all the sensors described above are output to the system control part 36. The system control part 36 controls all the motors described above.

Figure 2:
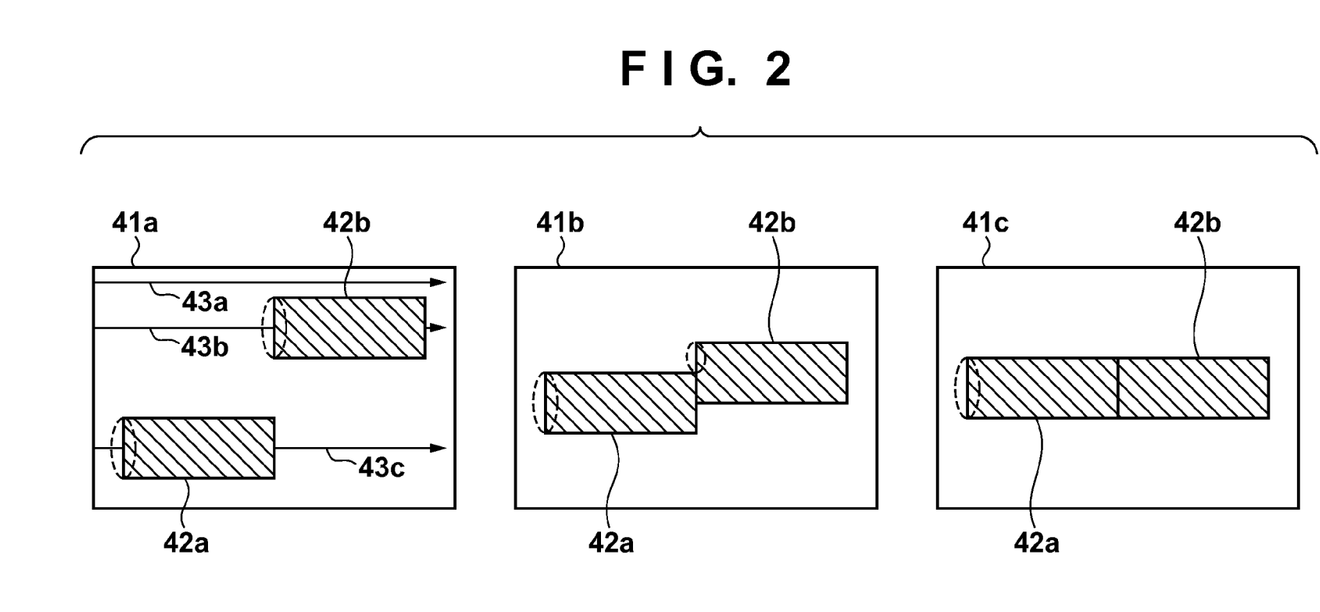
FIG. 2 is a diagram for explaining the first focal position detection method according to an embodiment.

FIG. 2 is a schematic view for explaining a focal position detection method using the detection of each focus index shift (to be referred to as a focal position detection method using focus indices hereinafter) as one of focal position detection methods in this embodiment. In other words, the shift of a focus index gives rise to information regarding focal position as will be discussed below. The focal position detection method using focus indices uses two focus indices generated by the split unit 22. This focal position detection method may be executed by, for example, the system control part 36. The split unit 22 moves on the optical axis in synchronism with the focus lens 28 to project two indices on the imaging device 31. A first focus index image 42a and a second focus index image 42b move in opposite directions with respect to each other as the split unit 22 moves along the optical axis. When the two indices coincide with each other (i.e. when the two focus indices moving toward each other in the vertical direction finally meet in the middle), focusing is understood to have been achieved. The illumination optical system 103 and in particular the split unit 22 is thus used to enable an examiner to know when focus has been achieved during the observation phase, but is no longer required once focus has been achieved and the fundus camera enters an imaging phase.

Images 41a and 41b in FIG. 2 show the states of the focus indices 42a and 42b when the split unit 22 moves in the optical axis. The examiner can observe both the first focus index 42a and the second focus index 42b in the same image.

Next will be described a method of calculating contrast values described with reference to FIG. 2 and a method of detecting a position where a focus index image shift is minimized by using contrast value differences depending on the positions of the first and second focus index images 42a and 42b. The detection of such positions will be described with reference to FIG. 3.

The image 41a shows the state of scanning for the evaluation of the contrast of the image. The contrast in this case indicates the luminance difference between adjacent pixels. A greater contrast value indicates a greater luminance difference. Scan lines are lines indicating a procedure for obtaining adjacent luminance values and are arranged in parallel and at a constant interval equal to a pixel interval. A contrast value is the value of the largest luminance difference in luminance data on the scan lines.

Referring to the image 41a, reference numerals 43a, 43b, and 43c denote examples of scan lines. In fact, there would be many more scan lines within an image than shown in image 41a. For example, a focus index such as 42a might overlap with 10 scan lines. A method of detecting contrast values in the focal position detection method using focus indices will be described with reference to these scan lines. This focal position detection method detects contrast values while focus indices are displayed. In this case, a focus index exhibits a higher luminance value than other fundus images such as a blood vessel image and so the luminance value difference between the focus index and the rest of the image can be interpreted as a contrast value. For the sake of descriptive convenience, we assume that the luminance value of each focus index image is constant, and the luminance value of a region other than the focus index image is also constant, but with a lower luminance value.

On the scan line 43a, the luminance is constant, because the first focus index image 42a and the second focus index image 42b are not included in the scan line. As a consequence, the contrast value on the scan line 43a is calculated as 0. On the scan line 43b, since the second focus index image 42b is included in the scan line, the luminance difference between the portion other than the index image and the left side surface of the second focus index image 42b (this "step" from background luminance to focus index luminance being shown as circled with a dotted line) is calculated as a contrast value on the scan line 43b. If, for example, the luminance of the portion other than the focus index is 0 and the luminance of the second focus index 42b is 100, the contrast value on the scan line 43b is 100. In addition, on the scan line 43c, the luminance difference at the left side surface of the first focus index image 42a is calculated as a contrast value on the scan line 43c. Like on the scan line 43b, the contrast value on the scan line 43c is 100.

The contrast value of the entire image 41a is then calculated by a number of scanning lines corresponding to the number of pixels in the vertical direction from the upper portion to the lower portion and adding the contrast values obtained on the respective lines. If, for example, the vertical length of each of the first focus index image 42a and the second focus index image 42b corresponds to 10 scan lines, the contrast value of the entire image 41a is calculated according to 100×10×2=2000. In this manner, the contrast value of the entire image is obtained. That is, the contrast values of the portions in the images 41a to 41c which are surrounded by the dotted lines are calculated as those of the respective images.

As described above, the contrast value of the image 41a is the sum of the contrast values of the entire focus index images 42a and 42b which are surrounded by the dotted lines in FIG. 2. Likewise, the contrast value of the image 41b is the sum of the contrast value of the entire focus index image 42a and the contrast value of ½ of the focus index image 42b. The contrast value of the image 41c is equal to that of the entire first focus index image 42a. Therefore, if, for example, the vertical length of first focus index image 42a and that of the second focus index image 42b each correspond to the same number of scan lines, i.e., 10 lines, the contrast value of the image 41a is 100×20=2000. Likewise, the contrast value of the image 41b is 100×15=1500, and the contrast value of the image 41c is 100×10=1000. That is, the image 41c has the smallest contrast value, the image 41b has the second largest contrast value, and the image 41a has the largest contrast value.

Figure 3:
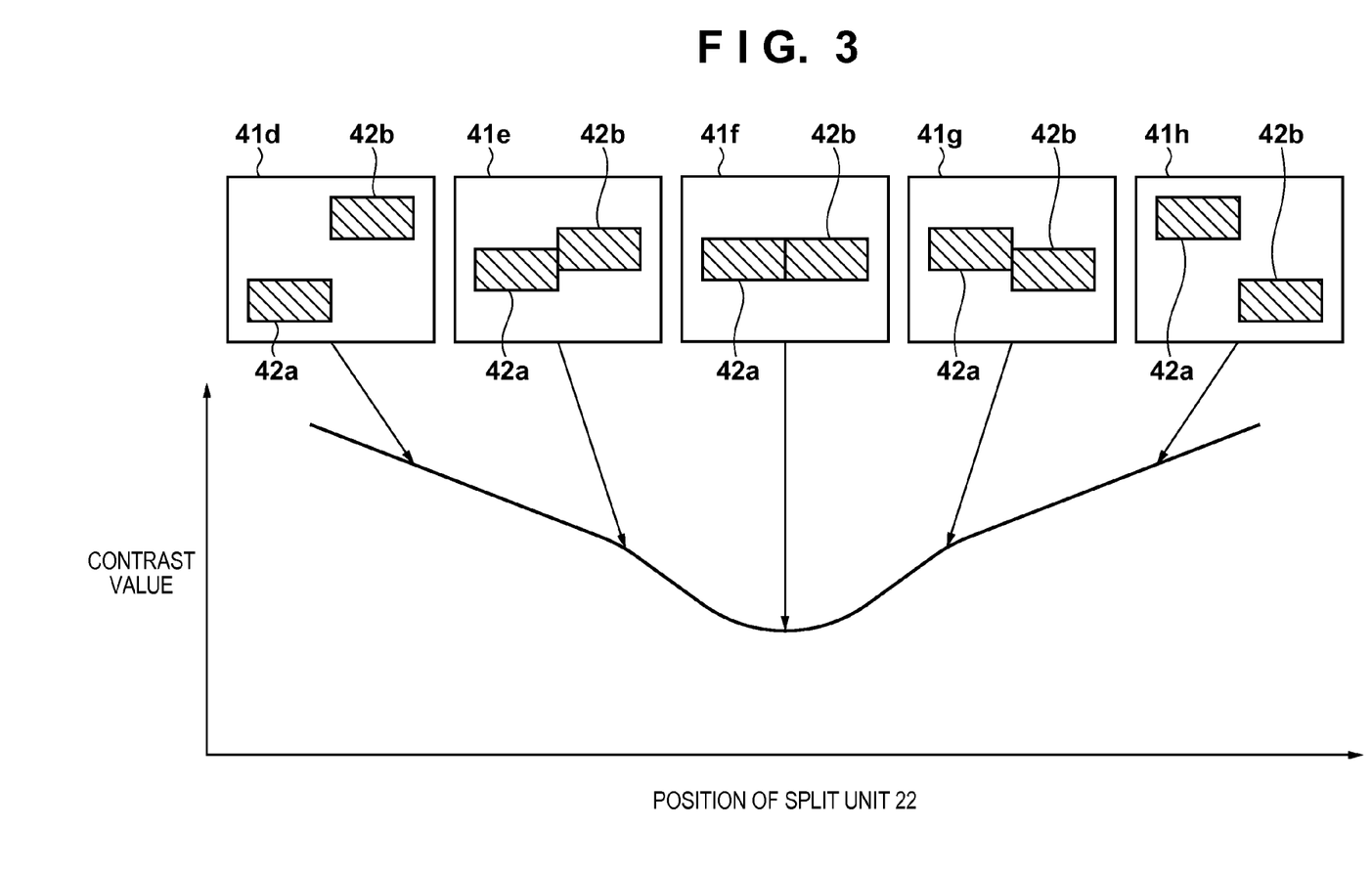
FIG. 3 is a diagram for explaining the first focal position detection method according to an embodiment.

Images 41d to 41h in FIG. 3 show the states of the focus index images obtained by the imaging device 31, like FIG. 2. The images 41d to 41h show focus index images when the split unit 22 is driven over its movable range, and in particular the states of the first and second focus index images 42a and 42b can be observed. The graph on the lower part of FIG. 3 shows the transition of contrast values relative to the position of the optical-axis direction of the split unit 22 when driven by the split shift driving motor M1. This graph shows a line connecting points corresponding to the contrast values obtained from the respective images 41d to 41h.

As described with reference to FIG. 2, the image 41f in which the shift between the focus index image 42a and the focus index image 42b is minimized exhibits the smallest contrast value. That is, the position of the split unit 22 at which the image 41f is obtained coincides with the position at which the focus index image shift is minimized. It is thus possible to perform focusing by detecting a position having the smallest of the contrast values obtained from the respective images 41d to 41h.

As described above, the focal position detection method using focus indices detects a focal position by using focus indices which are optically driven in synchronism with the focus lens 28. As described above, the focal position detection method using focus indices is a so-called split focusing scheme of calculating a focal position by evaluating the shift between split images (focus index images).

Figure 4:
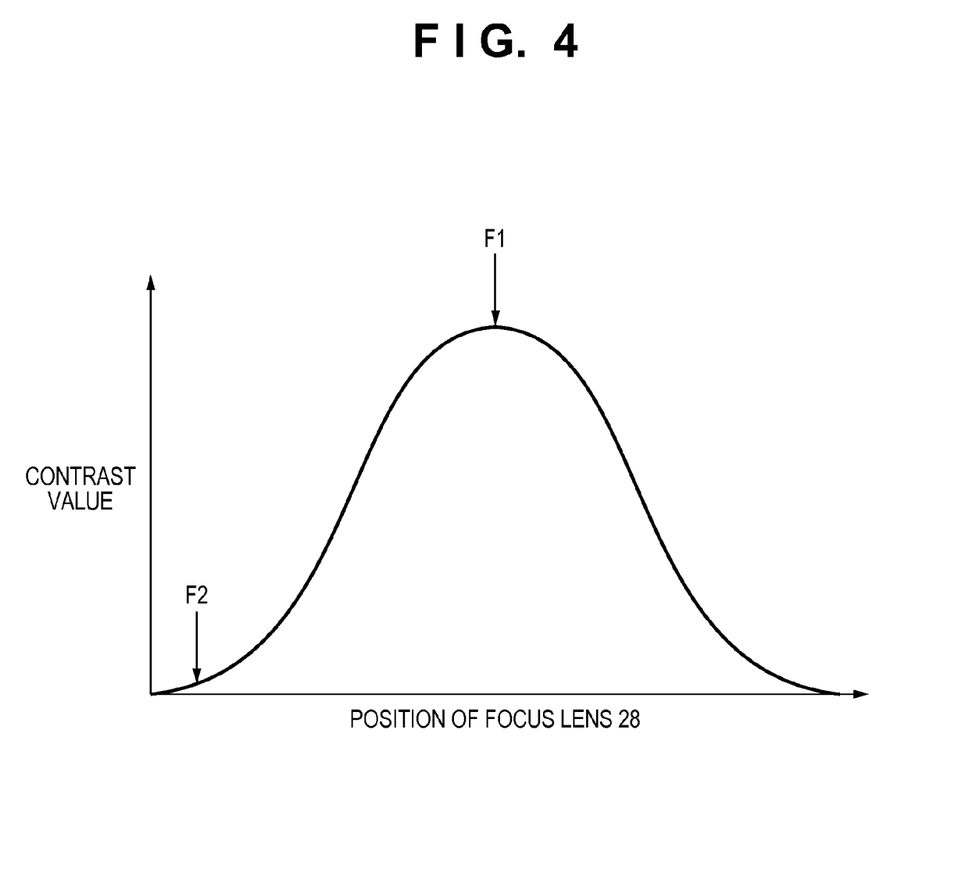
FIG. 4 is a graph for explaining the second focal position detection method according to an embodiment.

FIG. 4 is a graph for explaining a focal position detection method using contrast values as another focal position detection method in this embodiment. This focal position detection method performs focal position detection by evaluating the contrast value of an image of a medium and of a large artery peripheral portion on the retina. Note that the system control part 36 executes the focal position detection method using contrast values. The graph of FIG. 4 shows the position of the focus lens 28 moved in the optical-axis direction by the focus lens driving motor M3 and changes in the contrast value of the image signal obtained from the imaging device 31. The method of calculating contrast values is essentially the same as that used in the focal position detection method using focus indices described above, but without the focus indices. In the focal position detection method using focus indices, the differences in luminance between the left side surfaces of the focus index images 42a and 42b and the portion other than the index images are dominant as contrast components. In contrast, however, the focal position detection method using contrast values displays no focus index images. For this reason, in the focal position detection method using contrast values, the differences in luminance between a portion other than the medium and large artery on the retina and the two end portions of the medium and large artery are dominant as contrast components.

As shown in FIG. 4, since an image in an in-focus state becomes sharp, the contrast value is maximized at a focal position F1, whereas the contrast value is reduced at a position F2 where the amount of defocusing is large.

As described above, the focal position detection method using contrast values detects a focal position by calculating a position where an actually-captured image exhibits the highest contrast from the image itself. As described above, the focal position detection method using contrast values is a so-called contrast focusing scheme of calculating a focal position by evaluating the contrast of an image. Because contrast does not deteriorate with the insertion of a diopter correction lens, a focal position can be detected even if a diopter correction lens is inserted and the optical relationship between the focus lens 28 and the split unit 22 deteriorates.

Figure 5A:
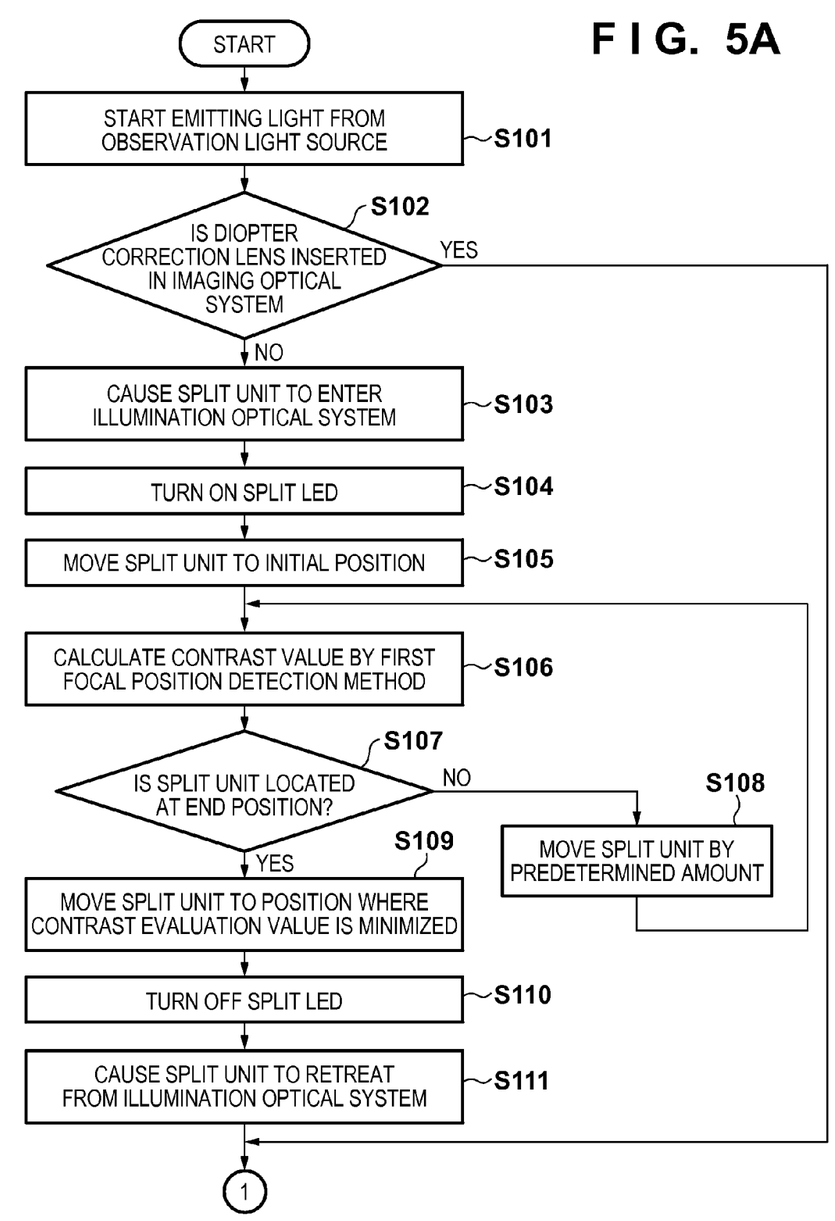
FIGS. 5A and 5B are flowcharts showing an imaging sequence in the fundus camera according to an embodiment.
Figure 5B:
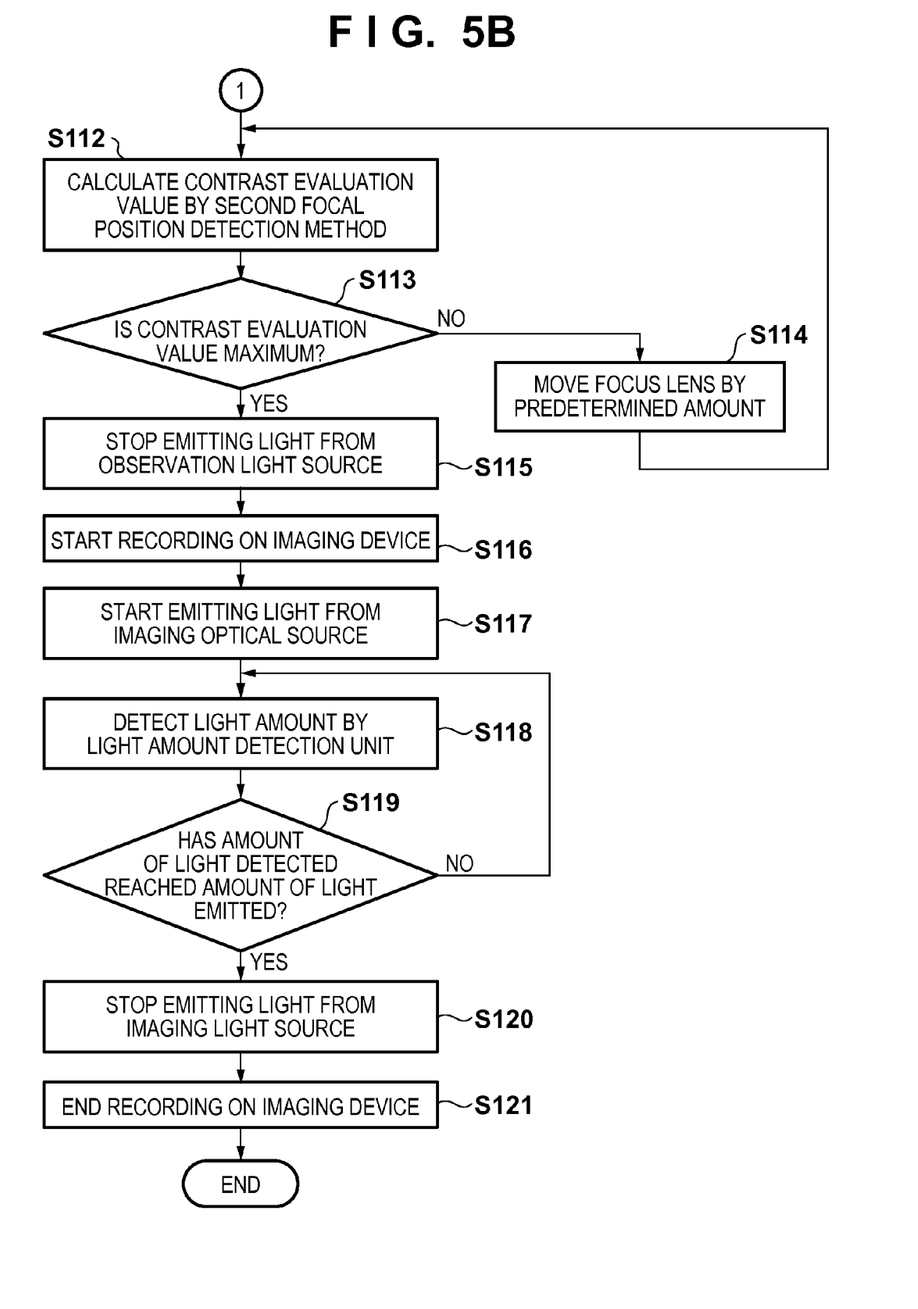

An imaging sequence in the fundus camera 100 will be described below with reference to the flowcharts of FIGS. 5A and 5B. When the examiner issues an instruction to start imaging via an operation part (not shown), the system control part 36 executes the processing in step S101 and the subsequent steps. First of all, in step S101, the system control part 36 turns on the observation light source 16. In step S102, the system control part 36 checks whether the diopter correction lens 29 has entered the imaging optical system 105. If the diopter correction lens 29 has not entered the imaging optical system 105, the process advances to step S103. If the diopter correction lens 29 has entered the imaging optical system 105, the process advances to step S112.

In step S103, the system control part 36 drives the split entering/retreating driving motor M2 to cause the split unit 22 to enter the illumination optical system 103. In step S104, the system control part 36 turns on the split LED 221. In step S105, the system control part 36 drives the split shift driving motor M1 to move the split unit 22 to an initial position. At this time, as described above, the focus lens 28 moves to the initial position in synchronism with the movement of the split unit 22. In step S106, the system control part 36 calculates a contrast value by the split focusing scheme described above with reference to FIGS. 2 and 3. In step S107, the system control part 36 checks whether the split unit 22 is at the end position. If the split unit 22 is not at the end position, the process advances to step S108. In step S108, the system control part 36 drives the split shift driving motor M1 to move the split unit 22 by a predetermined amount. After the movement, the process returns to step S106. At this time, since the split unit 22 moves in synchronism with the movement of the focus lens 28, the focus lens 28 also moves in accordance with the movement of the predetermined amount described above.

If the system control part 36 determines in step S107 that the split unit is at the end position, the process advances to step S109. In step S109, the system control part 36 drives the split shift driving motor M1 to move the split unit 22 to a position where the contrast value is minimized. In accordance with the movement of the split unit 22, the focus lens 28 also moves to the corresponding position. In step S110, the system control part 36 turns off the split LED 221. In step S111, the system control part 36 drives the split entering/retreating driving motor M2 to cause the split unit 22 to retreat from the illumination optical system 103.

In step S112, the system control part 36 calculates a contrast evaluation value by the contrast focusing scheme. In step S113, the system control part 36 determines whether the contrast evaluation value calculated in step S112 is maximized. If the contrast evaluation value is not maximized, the process advances to step S114. In step S114, the system control part 36 moves the focus lens 28 by a predetermined amount by using the focus lens driving motor M3. After the movement, the process returns to step S112.

If the system control part 36 determines in step S112 that the contrast evaluation value is at a maximum, the process advances to step S115. In step S115, the system control part 36 causes the observation light source 16 to stop emitting light. The system control part 36 causes the imaging device 31 to start recording in step S116. In step S117, the system control part 36 causes the imaging light source 12 to start emitting light. In step S118, the light amount detection part 11 detects a light amount. In step S119, the system control part 36 checks whether the light amount detected by the light amount detection part 11 in step S118 has reached a predetermined light amount. If the light amount has not reached the predetermined light amount, the process returns to step S118. If the light amount has reached the predetermined light amount, the process advances from step S119 to step S120. In step S120, the system control part 36 causes the imaging light source 12 to stop emitting light. In step S121, the system control part 36 stops recording operation by using the imaging device 31.

The fundus camera with the above arrangement can perform autofocus even in a state in which a diopter correction lens is inserted to image the fundus of a patient having strong myopia or hyperopia. That is, this camera can perform autofocus regardless of the presence/absence of a diopter correction lens. This facilitates imaging in a suitable in-focus state.

In the above processing, if the diopter correction lens 29 is not inserted in the optical path of the imaging optical system 105, the contrast focusing scheme is used after the use of the split focusing scheme. However, the present invention is not limited to this. If, for example, the diopter correction lens 29 is not inserted in the optical path of the imaging optical system 105, the camera might not perform focusing processing based on the contrast focusing scheme.

The above embodiment uses the contrast focusing scheme as the focal position detection method to be used when the diopter correction lens 29 is inserted (the focal position detection method to be executed in steps S112 to S114). However, the present invention is not limited to this. It is possible to use any scheme as long as it can evaluate focusing without using the split image. That is, when changing the focal position detection methods to be used by the system control part 36 in accordance with whether the diopter correction lens 29 is inserted in the optical path of the imaging optical system, this embodiment performs operation as follows:

when the diopter correction lens 29 is not inserted in the optical path, the embodiment uses the split focusing scheme of calculating a focal position by evaluating the shift between split images; and when the diopter correction lens 29 is inserted in the optical path, the embodiment uses the focusing scheme of detecting a focal position without using the split image.

As described above, the fundus camera according to the above embodiment can execute autofocus even in a state in which a diopter correction lens is inserted.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-237264, filed Oct. 26, 2012, which is hereby incorporated by reference herein in its entirety.

What is claimed is:
1. A fundus imaging apparatus comprising:
an illumination optical system configured to project illumination light on a fundus of an eye to be examined;
an imaging optical system configured to guide reflected light from the fundus to an imaging unit;
a driveable focus lens which is provided in an optical path of said imaging optical system and which is configured to focus the reflected light onto the imaging unit;
a focusing unit configured to detect a focal position of the reflected light based on a signal from said imaging unit and to drive the focus lens according to the detected focal position; and
a selection unit configured to select, from a plurality of different focal position detection methods, a focal position detection method used by said focusing unit, wherein a focal position detection method selected when a diopter correction lens is inserted in the optical path is different from a focal position detection method selected when the diopter correction lens is not inserted in the optical path.

2. The apparatus according to claim 1, wherein said selection unit is configured, when the diopter correction lens is not inserted in the optical path, to select a split focal position detection method of calculating a focal position of the reflected light by evaluating a shift between split images, and wherein said selection unit is configured, when the diopter correction lens is inserted in the optical path, to use a focal position detection method of detecting a focal position without using split images.

3. The apparatus according to claim 1, wherein said focusing unit is configured to use at least one of:

i) a split focal position detection method of evaluating a shift between split images; and ii) a contrast focal position detection method of evaluating a contrast of an image, and wherein said selection unit is configured to select between the split focal position detection method and the contrast focal position detection method in accordance with whether the diopter correction lens is inserted in the optical path.

4. The apparatus according to claim 3, wherein said selection unit is configured to select the focal position detection method to be used by said focusing unit so as to use the split focal position detection method and the contrast focal position detection method when the diopter correction lens is not inserted in the optical path and to use the contrast focal position detection method when the diopter correction lens is inserted in the optical path.

5. The apparatus according to claim 3, wherein said selection unit is configured to select the focal position detection method to be used by said focusing unit so as to select the split focusing method when the diopter correction lens is not inserted in the optical path and to select the contrast focusing method when the diopter correction lens is inserted in the optical path.

6. The apparatus according to claim 5, wherein the contrast focal position detection method evaluates a contrast of a fundus image.

7. The apparatus according to claim 5, wherein the contrast focal position detection method evaluates a contrast in a blood vessel portion.

8. A method of controlling a fundus imaging apparatus, the method comprising:

selecting, from a plurality of different focal position detection methods, a focal position detection method, wherein a focal position detection method selected when a diopter correction lens is inserted in an optical path of an imaging optical system that includes an imaging unit is different from a focal position detection method selected when the diopter correction lens is not inserted in the optical path; and detecting a focal position based on a signal from the imaging unit according to the selected focal position detection method.

9. A method according to claim 8, wherein the selecting step comprises selecting at least one of a split focal position detection method using split images for determining focal position and a contrast focal position detection method that does not use split images.

10. The method according to claim 8, wherein the selecting step selects a split focal position detection method of calculating a focal position of the reflected light by evaluating a shift between split images when a diopter correction lens is not inserted in the optical path, and wherein the selecting step selects a focal position detection method of detecting a focal position without using split images when the diopter correction lens is inserted in the optical path.

11. The method according to claim 8, wherein the detecting step uses at least one of:

i) a split focal position detection method of evaluating a shift between split images; and ii) a contrast focal position detection method of evaluating a contrast of an image, and wherein the selecting step selects between the split focal position detection method and the contrast focal position detection method in accordance with whether the diopter correction lens is inserted in the optical path.

12. The method according to claim 11, wherein the selecting step selects the focal position detection method to be used in the detecting step so as to use the split focal position detection method and the contrast focal position detection method when the diopter correction lens is not inserted in the optical path and to use the contrast focal position detection method when the diopter correction lens is inserted in the optical path.

13. The method according to claim 11, wherein the selecting step selects the focal position detection method to be used in the detecting step so as to select the split focusing method when the diopter correction lens is not inserted in the optical path and to select the contrast focusing method when the diopter correction lens is inserted in the optical path.

14. The method according to claim 13, wherein the contrast focal position detection method evaluates a contrast of a fundus image.

15. The method according to claim 13, wherein the contrast focal position detection method evaluates a contrast in a blood vessel portion.

16. A non-transitory computer-readable medium storing a program for causing a computer to execute a control method comprising:

selecting, from a plurality of different focal position detection methods, one focal position detection method, wherein a focal position detection method selected when a diopter correction lens is inserted in an optical path of an imaging optical system that includes an imaging unit is different from a focal position detection method selected when the diopter correction lens is not inserted in the optical path; and detecting a focal position based on a signal from the imaging unit according to the selected focal position detection method.

* * * * *